United States Patent [19]

Middleton

[11] 4,258,187

[45] Mar. 24, 1981

[54] PROCESS FOR PREPARING QUINAZOLINONE OXIDES

[75] Inventor: William J. Middleton, Chadds Ford, Pa.

[73] Assignee: E. I. Du Pont de Nemours and Company, Wilmington, Del.

[21] Appl. No.: 959,626

[22] Filed: Nov. 13, 1978

Related U.S. Application Data

[63] Continuation of Ser. No. 807,076, Jun. 16, 1977, abandoned.

[51] Int. Cl.³ .................. C07D 239/82; A61K 31/505
[52] U.S. Cl. ............................. 544/286; 260/239 BD; 260/245.5; 544/285; 564/50; 564/52
[58] Field of Search .......................................... 544/286

[56] References Cited

U.S. PATENT DOCUMENTS 3,923,803  12/1975  Inaba et al. .......................... 544/286
3,926,993  12/1975  Ishizumi et al. ...................... 544/286

OTHER PUBLICATIONS

Brown, *Fused Pyrimidines; Quinazalines;* Part I, pp. 78–80, 1967, Interscience.
Black, et al., "Synthesis", vol. 4, 1975, pp. 205–221.
Stamm, "Methodicum Chimicum", vol. 6, 1975, 329–401.

*Primary Examiner*—Donald G. Daus
*Assistant Examiner*—James H. Turnipseed

[57] ABSTRACT

Improved process for the preparation of 6-substituted-4-phenylquinazolinone 3-oxides. Such compounds are useful as intermediates in the preparation of 3-fluorobenzodiazepines, which are useful as tranquilizers, muscle relaxants and sedatives.

1 Claim, No Drawings

PROCESS FOR PREPARING QUINAZOLINONE OXIDES

This is a continuation of application Ser. No. 807,076, filed June 16, 1977, now abandoned.

BACKGROUND OF THE INVENTION

Copending U.S. patent application Ser. No. 687,318, filed May 26, 1976 by Elena M. Bingham and William Joseph Middleton, which is a continuation-in-part of U.S. patent application Ser. No 597,502, filed July 21, 1975, now abandoned, discloses certain novel 3-fluorobenzodiazepines of the formula:

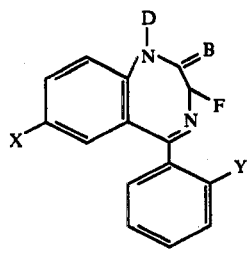

where
- X is Cl, Br, $NO_2$, or $CF_3$;
- Y is H, Cl, Br or F;
- D is H, hydrocarbyl of 1-4 carbons, $-CH_2CF_3$, $-CONHR$, $-CH_2CH_2NR_2$, or $-CH_2CH_2NR_2 \cdot A$, where R is alkyl of 1-4 carbons and A is a pharmaceutically suitable acid;
- B is O; or
- B and D together is $=N-N=C(R')-$ where $R'$ is H or $C_1-C_4$ alkyl, and the use of such compounds as tranquilizers, muscle relaxants and sedatives in mammals. In addition, Bingham and Middleton disclose a process for making such compounds by reaction of the corresponding 3-hydroxybenzodiazepine with a dialkylaminosulfur trifluoride as follows:

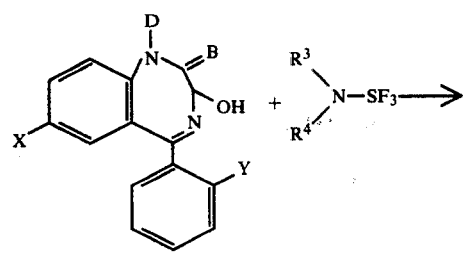

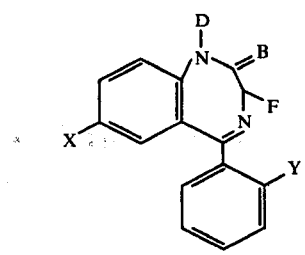

where $R^3$ and $R^4$ are a primary alkyl group of 1-4 carbons or taken together are $-(CH_2)_4-$ or $-(CH_2)_5$.

Copending U.S. patent application Ser. No. 807,075, filed on June 16, 1977 by William Joseph Middleton, now U.S. Pat. No. 4,182,760, discloses an improved process for preparing such 3-fluorobenzodiazepines, which improved process can be summarized schematically by the following equations:

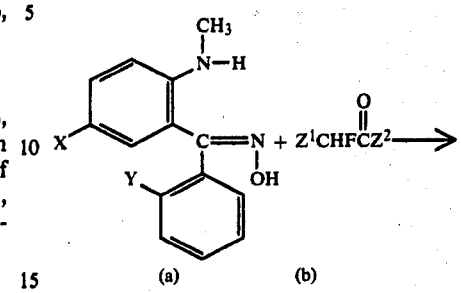

(a)    (b)

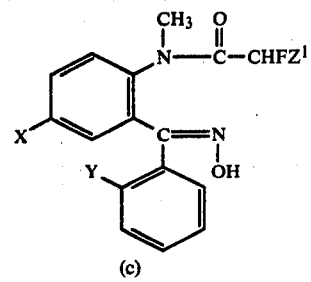

(c)

(c) + base (e.g. NaOH) $\longrightarrow$

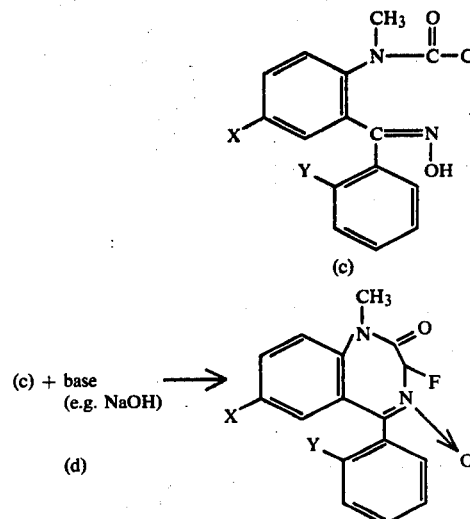

(d)

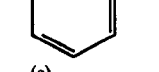

(e)

(e) + reducing agent [e.g.$P(OCH_3)_3$] $\longrightarrow$

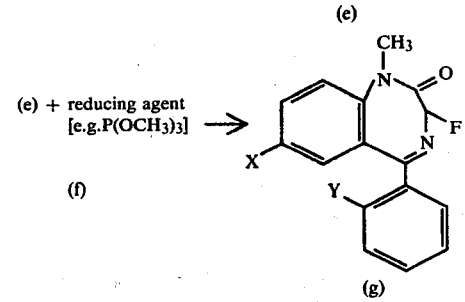

(f)

(g)

where
- X is Cl, Br, $NO_2$ or $CF_3$;
- Y is H, Cl, Br or F; and
- $Z^1$ and $Z^2$ are Cl or Br.

Middleton also discloses that starting material (1) can be prepared by the process disclosed in U.S. Pat. No. 3,398,139.

In addition, copending U.S. patent application Ser. No. 807,074, filed June 16, 1977 by Elena M. Bingham and Arthur J. Elliott, now U.S. Pat. No. 4,160,092, discloses an improved process for preparing the N-methylaminobenzophenone anti-oxime used as the starting material in Middleton's improved process discussed immediately above. The Bingham and Elliott process can be summarized schematically by the following equations:

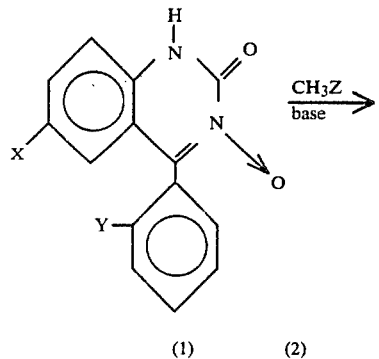

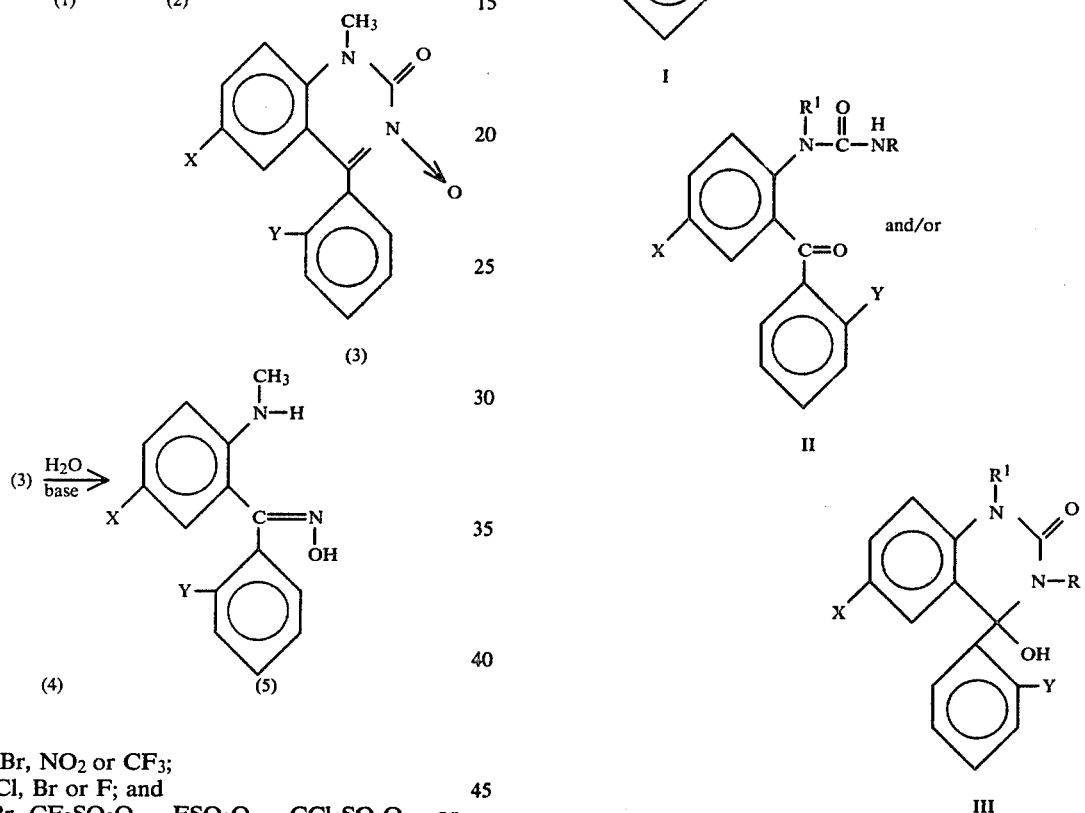

where
X is Cl, Br, NO$_2$ or CF$_3$;
Y is H, Cl, Br or F; and
Z is I, Br, CF$_3$SO$_2$O—, FSO$_2$O—, CCl$_3$SO$_2$O— or CH$_3$OSO$_2$O—.

Bingham and Elliott also disclose that the starting material quinazolinone 3-oxides can be prepared by a process taught by Sulkowski and Childress, J. Org. Chem., 27, 4424 (1962).

SUMMARY OF THE INVENTION

The present invention relates to an improved process for making the quinazolinone 3-oxides of formula (1), above, and an alternate process for making the quinazolinone 3-oxides of formula (3), above.

More specifically, the present invention relates to an improved process for preparing 6-substituted-4-phenyl-quinazolinone 3-oxides by the treatment of 2-aminobenzophenone-isocyanate reaction products with hydroxylamine salts.

Organic isocyanates of formula RNCO (where R is hydrocarbyl or halohydrocarbyl of 1–8 carbon atoms) react with 2-aminobenzophenones of formula I (X=Cl, Br, CF$_3$ or NO$_2$; Y=H, Br, Cl or F; R$^1$=H or CH$_3$) to give either ureas of the formula II or quinazolinones or formula III (X, Y and R$^1$ as previously defined), depending on the reaction conditions and the isocyanates used.

These reaction products (either or both II and III) can then be converted to quinazolinone oxides of formula IV by treating them with an acid salt of hydroxylamine.

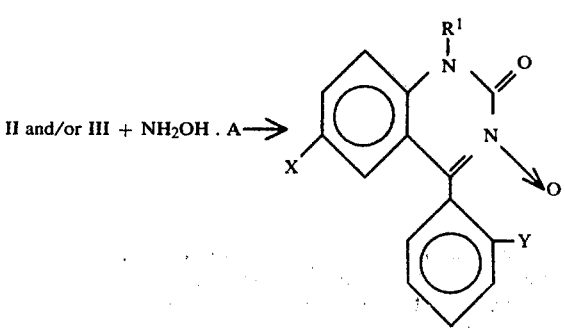

where A is an organic or inorganic acid with a pKa of less than 2.

DETAILED DESCRIPTION OF THE INVENTION

Process Conditions

Quinazolinone oxides of formula IV can be prepared by heating a solution or mixture of 2-aminobenzophenone-isocyanate reaction products (of Formula II or III) and an acid addition salt of hydroxylamine in an alcohol solvent. The reaction is conveniently carried out at the reflux temperature of the alcohol solvent, but temperatures from 40° to 200° C. are operable. Alcohol solvents useful for this reaction include, but are not limited to, ethanol, methanol, propanol, isopropanol, butanol, 2-methoxyethanol, ethylene glycol, and propylene glycol. Salts of hydroxylamine useful in this reaction include salts with organic or inorganic acids having a pKa of less than 2, such as hydroxylamine hydrochloride, hydroxylamine hydrobromide and hydroxylamine sulfate. The time required for the reaction varies from a few minutes when more reactive isocyanate adducts or higher boiling alcohols are used, to a few days or even weeks when less reactive isocyanate adducts or lower boiling alcohols are used.

The product quinazolinone oxides can be isolated from the reaction mixture by conventional means. In most cases, the quinazolinone oxides are considerably less soluble than the reactants, and will precipitate during the course of the reaction. When this occurs, the product quinazolinone oxides can be isolated by simply filtering the reaction mixture.

The 2-aminobenzophenone-isocyanate adducts used as starting material can be prepared by the reaction of 2-aminobenzophenones with organic isocyanates as illustrated in the following Examples or as described by Sulkowski et al., J. Org. Chem., 27, 4424 (1962) or by Metlesics et al., J. Org. Chem., 31, 1007 (1966).

Alternatively, the compounds of formula IV can be prepared by heating a compound of formula II in a suitable alcohol followed by treatment with a suitable acid addition salt of hydroxylamine.

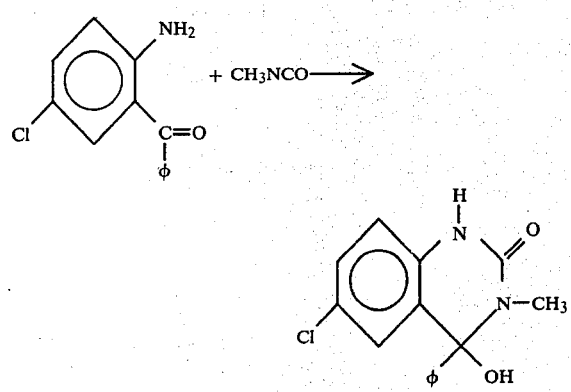

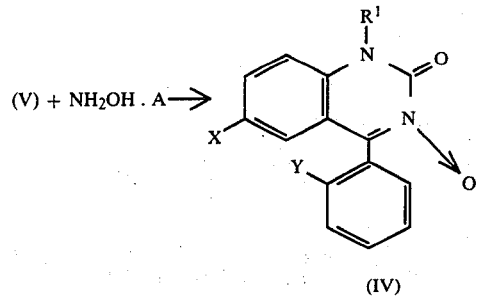

where $R^2OH$ is a lower aliphatic alcohol of 1–6 carbon atoms, preferably methanol or ethanol.

EXAMPLE 1

Part A.
6-Chloro-3,4-dihydro-4-hydroxy-3-methyl-4-phenyl-2(1H)-quinazolinone

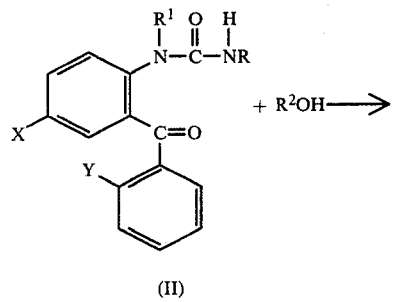

A solution of 100 g (0.43 mole) of 2-amino-5-chlorobenzophenone and 40 g (0.7 mole) of methyl isocyanate in 300 ml of methylene chloride was refluxed for two days and then cooled. The solid portion of the reaction mixture was collected on a filter and washed with methylene chloride to give 119.8 g (96% yield) of 6-chloro-3,4-dihydro-4-hydroxy-3-methyl-4-phenyl-2(1H)-quinazolinone as a white crystalline powder: mp 296°–298° (dec); $^1$H nmr (DMSO-d$_6$), δ 2.66 ppm (s, 3H), 6.8–7.6 ppm (m, 8H) and 10.0 ppm (s, NH); $^{13}$C nmr (DMSO-d$_6$) δ 86.6 ppm (for COH) and 151.4 ppm (for NHCO).

Anal. Calcd for $C_{15}H_{13}ClN_2O_2$: C, 62.39; H, 4.54; N, 9.70; Found: C, 62.10; H, 4.67; N, 9.53.

Part B. 6-Chloro-4-phenyl-2(1H)-quinazolinone 3-Oxide

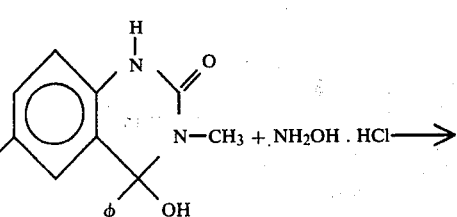

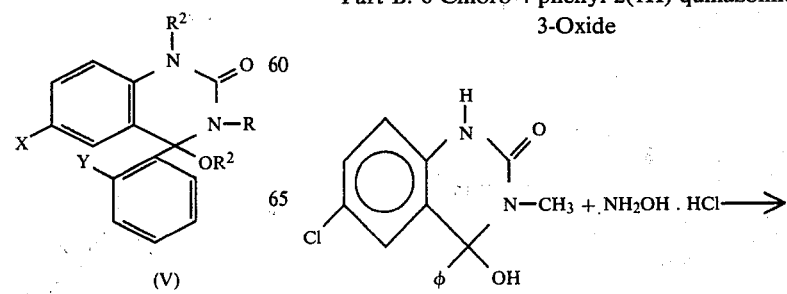

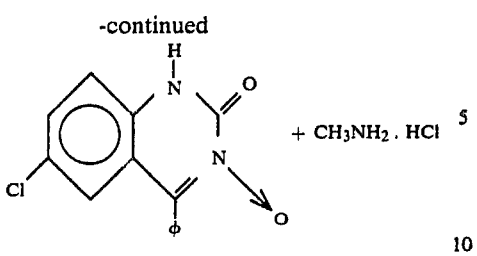

A stirred mixture of 86.6 g (0.3 mole) of 6-chloro-3,4-dihydro-4-hydroxy-3-methyl-4-phenyl-2(1H)-quinazolinone and 62.5 g (0.9 mole) of hydroxylamine hydrochloride in 1500 ml ethanol was refluxed for 187 hr, and then cooled. The solid portion of the reaction mixture was collected on a filter, washed with ethanol, and dried in air to give 67.9 g (83%) of 6-chloro-4-phenyl-2(1H)-quinazolinone 3-oxide as yellow crystals: mp 267°–269°.

EXAMPLE 2

Part A.
6-Chloro-3-ethyl-3,4-dihydro-4-hydroxy-4-phenyl-2(1H)-quinazolinone

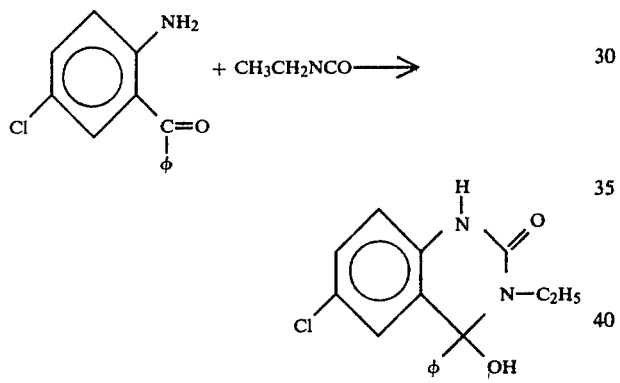

A solution of 28.4 g (31.7 ml, 0.4 mole) of ethyl isocyanate and 46.3 g (0.2 mole) of 2-amino-5-chlorobenzophenone in 100 ml of methylene chloride was refluxed for 20 hr. The reaction mixture was cooled, and the solid portion was collected on a filter and washed with methylene chloride to give 50.72 g (84%) of 6-chloro-3-ethyl-3,4-dihydro-4-hydroxy-4-phenyl-2(1H)-quinazolinone as colorless crystals: mp 182°–184°; $^{13}$C nmr (DMSO-d$_6$) δ 86.9 ppm (for COH) and δ 151.0 ppm (for NHCO).

Anal. Calcd for C$_{16}$H$_{15}$ClN$_2$O$_2$: C, 63.47; H, 4.99; N, 9.25. Found: C, 63.29; H, 4.83; N, 9.46.

Part B. 6-Chloro-4-phenyl-2(1H)quinazolinone 3-Oxide

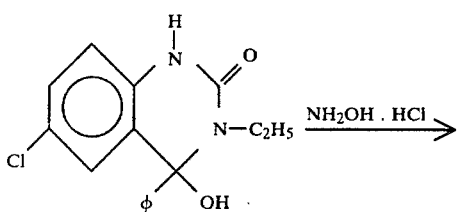

A stirred mixture of 12.11 g (0.04 mole) of 6-chloro-3-ethyl-3,4-dihydro-4-hydroxy-4-phenyl-2(1H)quinazolinone and 8.34 g (0.12 mole) of hydroxylamine hydrochloride in 200 ml ethanol was refluxed for 3 days and then cooled. The solid portion of the reaction mixture was collected on a filter, washed with ethanol, and dried to give 9.27 g (85%) of 6-chloro-4-phenyl-2(1H)quinazolinone 3-oxide as yellow crystals, mp 267°–269°.

EXAMPLE 3

Part A.
6-Chloro-3,4-dihydro-4-hydroxy-1,3-dimethyl-4-phenyl-2(1H)-quinazolinone

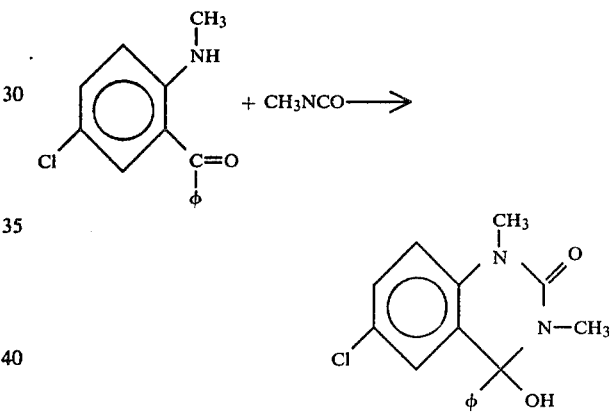

A solution of 12.3 g (0.05 mole) of 5-chloro-2-methylaminobenzophenone and 6 ml (0.1 mole) of methyl isocyanate in 50 ml of methylene chloride was refluxed for 3 days, and then cooled. The solid portion of the reaction mixture was collected on a filter and washed with methylene chloride to give 7.05 g (47%) of 6-chloro-3,4-dihydro-4-hydroxy-1,3-dimethyl-4-phenyl-2(1H)-quinazolinone as light yellow crystals; mp 174°–176°; $^1$H nmr (DMSO-d$_6$) δ 2.67 ppm (s, 3H), 3.38 ppm (s, 3H), 6.8–7.7 ppm (m, 9H).

Anal. Calcd for C$_{16}$H$_{15}$ClN$_2$O$_2$: C, 63.47; H, 4.99; N, 9.25. Found: C, 63.44; H, 4.96; N, 8.84.

Part B.
6-Chloro-1-methyl-4-phenyl-2(1H)-quinazolinone 3-Oxide

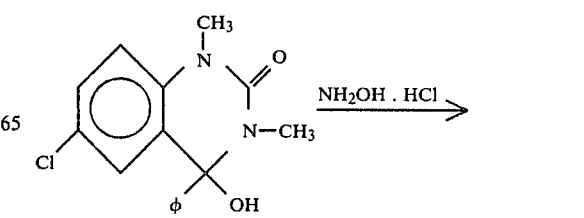

-continued

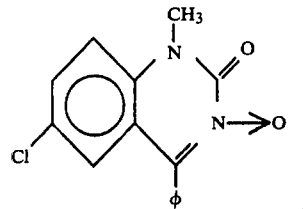

A stirred mixture of 3.03 g (0.01 mole) of 6-chloro-3,4-dihydro-4-hydroxy-1,3-dimethyl-4-phenyl-2(1H)-quinazolinone and 2.09 g (0.03 mole) of hydroxylamine hydrochloride in 50 ml of ethanol was refluxed for 5 days. The reaction mixture was cooled, and the solid portion was collected on a filter, washed with ethanol, and dried in air to give 1.75 g (61%) of 6-chloro-1-methyl-4-phenyl-2-(1H)-quinazolinone 3-oxide as yellow crystals: mp 289°-291°; $^1$H nmr (TFA) δ4.22 ppm (s, 3H) and 7.6-8.5 ppm (m, 8H).

EXAMPLE 4

Part A. 1-(2-Benzoyl-4-chlorophenyl)-3-isopropylurea

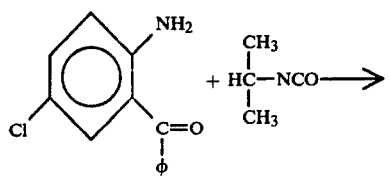

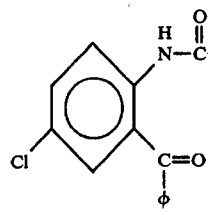

A mixture of 14 g (0.06 mole) of 2-amino-5-chlorobenzophenone and 40 ml of isopropyl isocyanate was refluxed for 3 hrs. The solid that formed was suspended in 25 ml of hexane, and then collected on a filter and recrystallized from ethanol to give 12.0 g (63%) of 1-(2-benzoyl-4-chlorophenyl)-3-isopropylurea as colorless needles: mp 190°-192°; $^1$H nmr (CDDl$_3$) δ1.19 ppm (d, J=6 Hz, 6H), 3.98 ppm (m, 1H), 4.95 ppm (m, NH), 7.2-7.8 ppm (m, 7H), 8.5 ppm (d, J=10 Hz, 1H) and 10.1 ppm (NH); $^{13}$C nmr (DMSO-d$_6$) δ195.4 ppm (C=O) and 153.9 ppm (NHCO).

Anal. Calcd for C$_{17}$H$_{17}$ClN$_2$O$_2$: C, 64.45; H, 5.41; N, 8.85. Found: C, 64.21; H, 5.40; N, 8.78.

Part B. 6-Chloro-4-phenyl-2(1H)-quinazolinone 3-Oxide

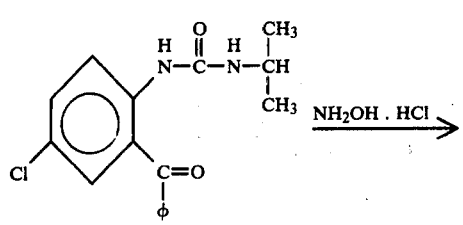

-continued

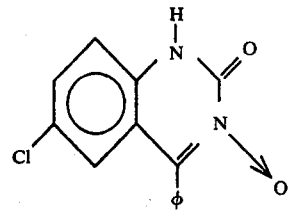

A stirred mixture of 6.34 g (0.02 mole) of 1-(2-benzoyl-4-chlorophenyl)-3-isopropylurea and 4.17 g (0.06 mole) of hydroxylamine hydrochloride in 100 ml of ethanol was refluxed for 48 hr, and then cooled. The suspended crystals were collected on a filter, washed with alcohol, and then dried in air to give 4.60 g (84%) of 6-chloro-4-phenyl-(2(1H)-quinazolinone 3-oxide as yellow crystals, mp 267°-269° (dec.).

EXAMPLE 5

Part A. 1-(2-Benzoyl-4-chlorophenyl)-3-phenylurea

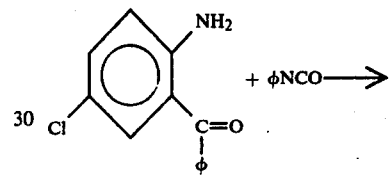

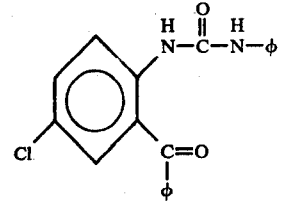

A solution of 13.1 g (0.11 mole) of phenyl isocyanate and 23.17 g (0.1 mole) of 2-amino-5-chlorobenzophenone in 70 ml of methylene chloride was refluxed for 20 hr, and then evaporated to dryness under reduced pressure. The residue was recrystallized from ethanol to give 31.71 g (90%) of 1-(2-benzoyl-4-chlorophenyl)-3-phenylurea as colorless crystals: mp 145°-147°; $^1$H nmr (DMSO-d$_6$) δ6.7-8.3 ppm (m, 13H), 9.43 ppm (d, J=7 Hz, 1H, exD$_2$O) and 10.25 ppm (s, 1H, exD$_2$O); $^{13}$C nmr (DMSO-d$_6$) δ152.2 ppm (NHCO) and 195.5 ppm (C=O).

Anal. Calcd for C$_{20}$H$_{15}$ClN$_2$O$_2$: C, 68.21; H, 4.50; N, 8.02. Found: C, 68.21; H, 4.50; N, 8.02.

Part B. 6-Chloro-4-phenyl-2(1H)-quinazolinone 3-Oxide

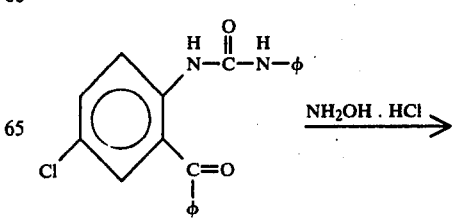

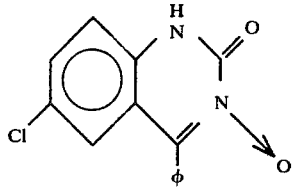

A stirred mixture of 7.02 g (0.02 mole) of 1-(2-benzoyl-4-chlorophenyl)-3-phenylurea and 4.17 g (0.06 mole) of hydroxylamine hydrochloride in 100 ml of ethanol was refluxed for 22 hr, and then cooled. The suspended solid was collected on a filter, washed with ethanol, and dried in air to give 3.82 (70%) of 6-chloro-4-phenyl-2(1H)-quinazolinone as yellow crystals; mp 267°–269°.

EXAMPLE 6
Part A.
1-(2-Benzoyl-4-chlorophenyl)-1-methyl-3-phenylurea

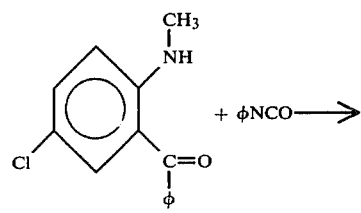

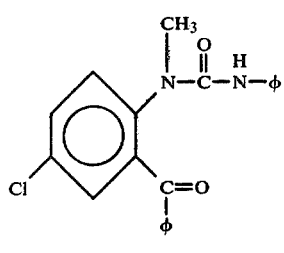

A solution of 12.3 g (0.05 mole) of 5-chloro-2-methylaminobenzophenone and 11.9 g (0.1 mole) of phenyl isocyanate in 50 ml of methylene chloride was refluxed for 3 days, and then evaporated to dryness under reduced pressure. The residual syrup was stirred with ether until it crystallized. The crystals were collected on a filter and washed with ether to give 12.06 g (66%) of 1-(2-benzoyl-4-chlorophenyl)-1-methyl-3-phenylurea as light yellow crystals. A sample was recrystallized from ethanol to give colorless crystals: mp 158°–160°; $^1$H nmr (DMSO-d$_6$) δ3.41 ppm (s, 3H), 6.7–7.5 ppm (m, 13H).

Anal. Calcd for $C_{21}H_{17}ClN_2O_2$: C, 69.13; H, 4.70; N, 7.68. Found: C, 68.82; H, 4.73; N, 7.48.

Part B.
6-Chloro-1-methyl-4-phenyl-2-(1H)quinazolinone 3-Oxide

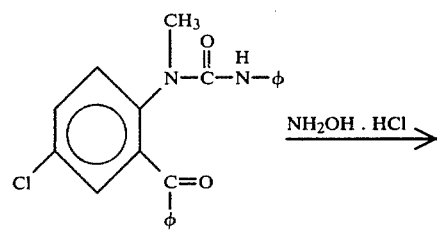

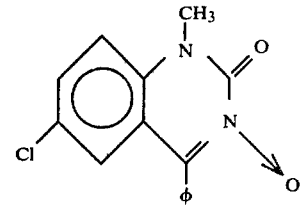

A mixture of 3.65 g (0.01 mole) of 1-(2-benzoyl-4-chlorophenyl)-1-methyl-3-phenylurea and 2.09 g (0.03 mole) of hydroxylamine hydrochloride in 50 ml of ethanol was stirred and refluxed for 5 days. The reaction mixture was cooled, and the suspended solid was collected on a filter, washed with alcohol, and dried in air to give 1.80 g (63%) of 6-chloro-1-methyl-4-phenyl-2-(1H)-quinazolinone as yellow crystals, mp 289°–291°.

EXAMPLE 7
Part A.
6-Chloro-4-ethoxy-3,4-dihydro-3,4-diphenyl-2(1H)-quinazolinone

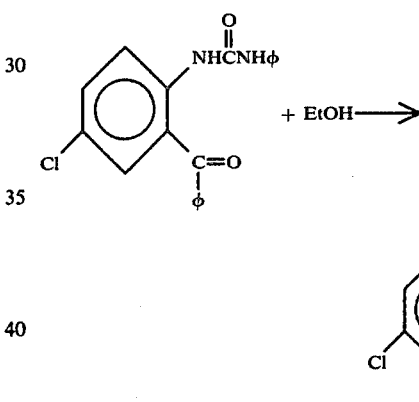

A solution of 10.0 g (0.285 mole) of 1-(2-benzoyl-4-chlorophenyl)-3-phenylurea in 50 ml ethanol was refluxed for 18 hr, and then cooled. The solid that formed was collected on a filter and washed with ethanol to give 9.46 g (88%) of 6-chloro-4-ethoxy-3,4-dihydro-3,4-diphenyl-2(1H)-quinazolinone as colorless crystals: mp 209°–211°. The $^1$H nmr spectrum shows the presence of an ethyl group in addition to aromatic hydrogens.

Anal. Calcd for $C_{22}H_{19}ClN_2O_2$: C, 69.74; H, 5.05; N, 7.40. Found: C, 70.12; H, 5.05; N, 7.35.

Part B. 6-Choro-4-phenyl-2-(1H)-quinazolinone 3-Oxide

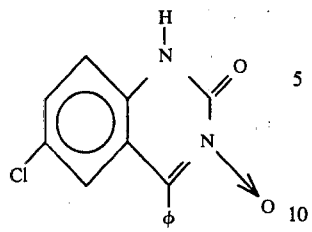

A mixture of 3.51 g (0.0093 mole) of 6-chloro-4-ethoxy-3,4-dihydro-3,4-diphenyl-2(1H)-quinazolinone and 2.09 g (0.03 mole) of hydroxylamine hydrochloride in 50 ml alcohol was refluxed for 4 days, and then cooled. The solid that formed was collected on a filter, washed with ethanol, and dried in air to give 1.82 g (72%) of 6-chloro-4-phenyl-2(1H)-quinazolinone 3-oxide as yellow crystals, mp 267°–269°.

EXAMPLE 8

6-Chloro-4-phenyl-2(1H)-quinazolinone 3-Oxide

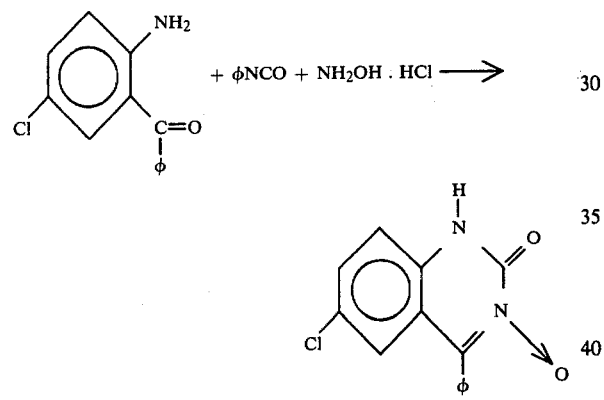

A mixture of 12.6 g (0.05 mole) of 2-amino-5-chlorobenzophenone and 6.55 g (0.055 mole) of phenyl isocyanate was heated on a steam-bath for 30 min., and then 250 ml ethanol and 10.43 g (0.15 mole) of hydroxylamine hydrochloride were added and mixture was refluxed for 2 days and then cooled. The solid precipitate that formed was collected on a filter, washed with ethanol, and dried in air to give 9.42 g (69%) of 6-chloro-4-phenyl-2(1H)-quinazolinone 3-oxide as yellow crystals, mp 267°–269°.

EXAMPLE 9

6-Chloro-4-phenyl-2(1H)-quinazolinone 3-Oxide

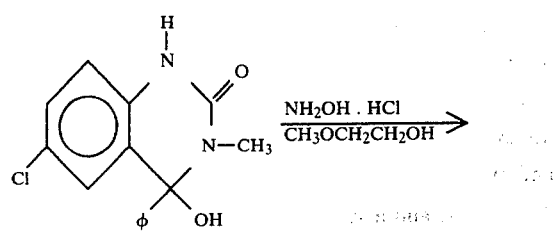

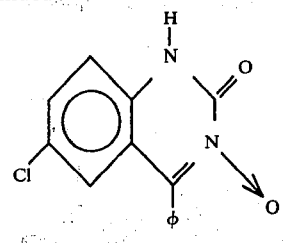

A stirred mixture of 2.89 g (0.01 mole) of 6-chloro-3,4-dihydro-4-hydroxy-3-methyl-4-phenyl-2(1H)-quinazolinone and 2.09 g (0.03 mole) of hydroxylamine hydrochloride in 50 ml of 2-methoxyethanol (ethylene glycol monomethyl ether) was refluxed for 2 hours, and then cooled to 0°. The solid that formed was collected on a filter, washed with ethanol, and dried in air to give 1.40 g (51%) of 6-chloro-4-phenyl-2(1H)-quinazolinone 3-oxide as yellow crystals, mp 267°–269°.

EXAMPLE 10

Part A.
6-Bromo-3,4-dihydro-4-hydroxy-3-methyl-4-phenyl-2(1H)-quinazolinone

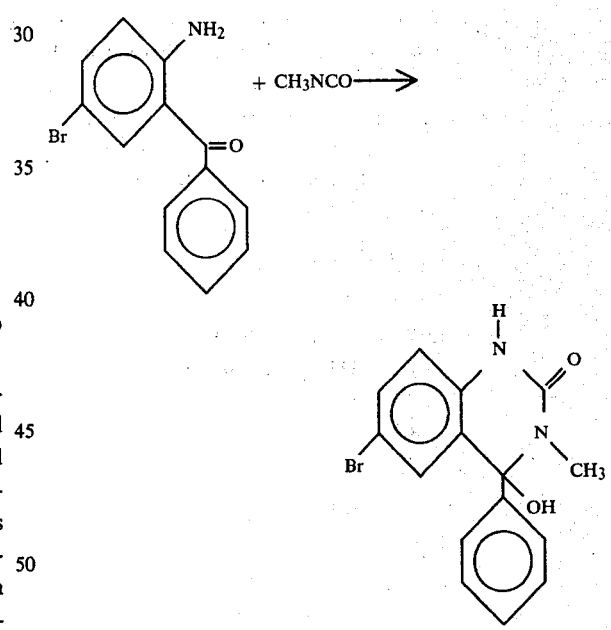

A solution of 14.70 g (0.053 mole) of 2-amino-5-bromobenzophenone and 6.0 g (0.21 mole) of methyl isocyanate in 75 ml of methylene chloride was refluxed for two days and then cooled. The solid portion of the reaction mixture was collected on a filter and washed with methylene chloride to give 16.18 g (90% yield) of 6-bromo-3,4-dihydro-4-hydroxy-3-methyl-4-phenyl-2(1H)-quinazolinone as a white crystalline powder: mp 293°–294° (dec.).

$^1$H nmr (DMSO-$d_6$) $\delta$2.66 ppm (s, 3H), 6.5–7.5 ppm (m, 8H).

Anal. Calcd for $C_{15}H_{13}BrN_2O_2$: C, 54.07; H, 3.93; N, 8.41. Found: C, 54.24; H, 3.89; N, 8.12.

Part B. 6-Bromo-4-phenyl-2(1H)-quinazolinone 3-Oxide

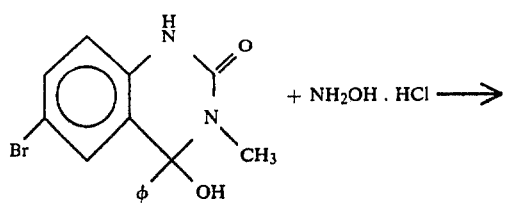
+ NH₂OH . HCl ⟶

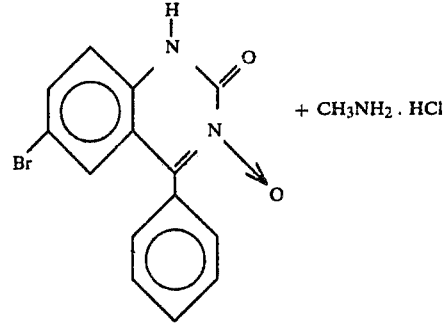
+ CH₃NH₂ . HCl

A stirred mixture of 28.28 g (0.085 mole) of 6-bromo-3,4-dihydro-4-hydroxy-3-methyl-4-phenyl-2(1H)-quinazolinone and 17.6 g (0.25 mole) of hydroxylamine hydrochloride in 425 ml of ethanol was refluxed for 192 hours and then cooled. The solid portion of the reaction mixture was collected on a filter, washed with ethanol, and dried in air to give 20.92 g (0.066 mole, 78%) of 6-bromo-4-phenyl-2(1H)-quinazolinone 3-oxide as light yellow crystals: mp 275°–276°.

EXAMPLE 11

Part A.
6-Chloro-3-ethyl-4-(2-fluorophenyl)-3,4-dihydro-4-hydroxy-2(1H)-quinazolinone

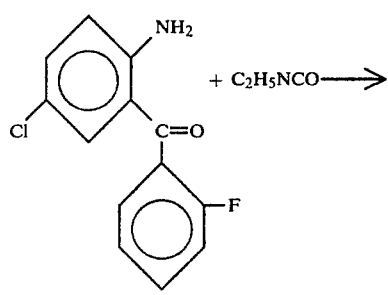
+ C₂H₅NCO ⟶

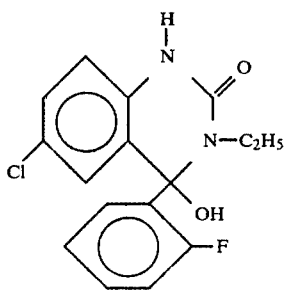

A mixture of 25 g (0.1 mole) of 2-amino-5-chloro-2'-fluorobenzophenone and 35.5 g (0.5 mole) of ethyl isocyanate was refluxed for 20 hr, and then cooled. The solid portion of the reaction mixture was collected on a filter and washed with methylene chloride to give 19.6 g (61%) of 6-chloro-3-ethyl-4-(2-fluorophenyl)-3,4-dihydro-4-hydroxy-2(1H)-quinazoline as a white crystalline powder: mp 176°–178° (dec.); $^{19}$F nmr (DMSO-d₆)—114.0 ppm; ir (KBr) at 6.24μ for C=O.

Anal. Calcd for C₁₆H₁₄ClFN₂O₂: C, 59.92; H, 4.40; N, 8.73. Found: C, 60.11; H, 4.44; N, 8.83.

Part B.
6-Chloro-4-(2-fluorophenyl)-2(1H)-quinazolinone 3-Oxide

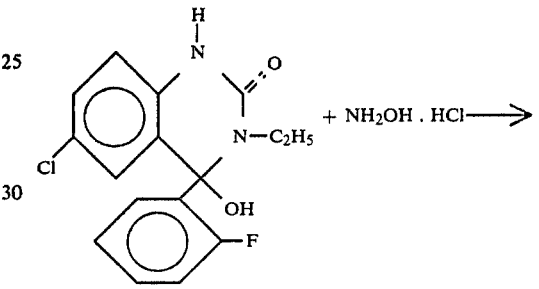
+ NH₂OH . HCl ⟶

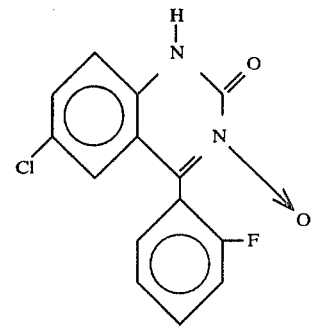

A stirred mixture of 18.0 g (0.056 mole) of 6-chloro-3-ethyl-4-(2-fluorophenyl)-3,4-dihydro-4-hydroxy-2(1H)-quinazoline, 11.8 g (0.17 mole) of hydroxylamine hydrochloride, and 280 ml of ethanol was refluxed for 3 days. The reaction mixture was cooled, and the precipitate was collected on a filter and washed with ethanol to give 6.67 g (47%) of 6-chloro-4-(2-fluorophenyl)-2(1H)-quinazoline 3-oxide as a yellow crystalline powder; mp 268°–270° (dec.); $^{19}$F nmr (DMSO-d₆) δ111.1 ppm.

Anal. Calcd for C₁₄H₈ClFN₂O₂: C, 57.85; H, 2.77; N, 9.64. Found: C, 58.01; H, 2.83; N, 9.59.

Table I shows additional ureas and hydroxyquinazolinones which can be prepared by the process disclosed and exemplified above using the appropriate aminobenzophenone and a suitable organic isocyanate.

TABLE I
Preparation of Substituted Ureas and Hydroxyquinazolinones

| Aminobenzophenone | Organic Isocyanate | Product |
|---|---|---|
| 2-amino-5-bromo-2'-fluorobenzophenone | + Cl—C₆H₄—NCO → | N-(2-(2-fluorobenzoyl)-4-bromophenyl)-N'-(4-chlorophenyl)urea |
| 2-(methylamino)-5-chloro-2'-chlorobenzophenone | + C₂H₅NCO → | 1-methyl-3-ethyl-4-(2-chlorophenyl)-4-hydroxy-6-chloro-hydroxyquinazolinone |
| 2-(methylamino)-5-trifluoromethylbenzophenone | + CH₃NCO → | 1,3-dimethyl-4-phenyl-4-hydroxy-6-trifluoromethyl-hydroxyquinazolinone |
| 2-amino-5-trifluoromethylbenzophenone | + C₆H₁₁—NCO → | N-(2-benzoyl-4-trifluoromethylphenyl)-N'-cyclohexylurea |

Table II shows additional quinazolinone oxides which can be prepared by the process disclosed and exemplified above using the appropriate isocyanate adduct and hydroxylamine or a suitable salt thereof.

TABLE II
Preparation of Selected Quinazolinone Oxides

| Isocyanate Adduct | Hydroxylamine | Quinazolinone Oxide |
|---|---|---|
| N-(2-(2-fluorobenzoyl)-4-bromophenyl)-N'-(4-chlorophenyl)urea | + NH₂OH · HCl → | 7-bromo-5-(2-fluorophenyl)quinazolinone-2(1H)-one 4-oxide |

TABLE II-continued
Preparation of Selected Quinazolinone Oxides

| Isocyanate Adduct | Hydroxylamine | Quinazolinone Oxide |
|---|---|---|

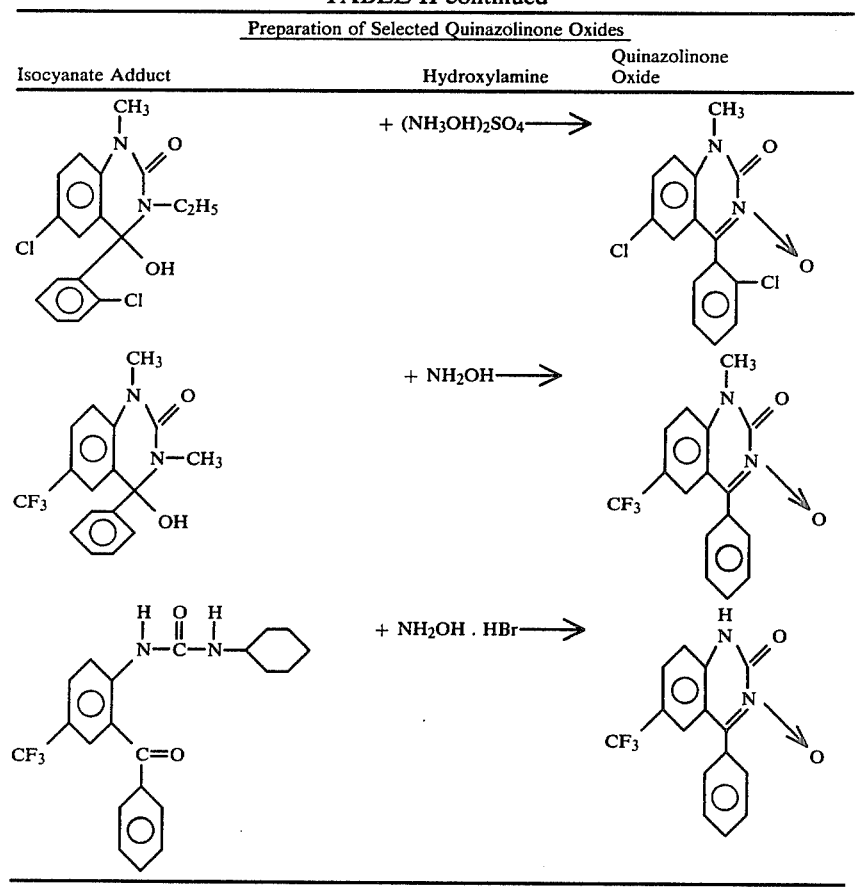

I claim:

1. A process for preparing a compound of the formula:

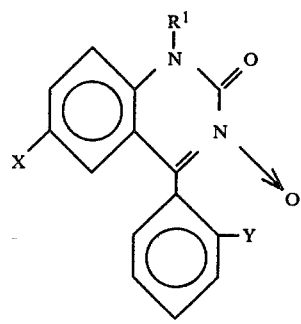

where
X is Cl, Br, $NO_2$ or $CF_3$;
Y is H, Br, Cl or F; and
$R^1$ is H or $CH_3$;
which comprises treating either or both of the compounds of the formulae:

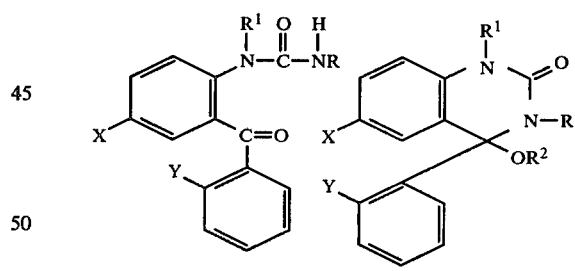

with an acid salt of hydroxylamine, where
R is hydrocarbyl or halohydrocarbyl of up to 8 carbon atoms, and
$R^2$ is H or alkyl or 1–6 carbon atoms.

* * * * *